United States Patent [19]

Goodman

[11] Patent Number: 4,746,651

[45] Date of Patent: May 24, 1988

[54] ANTIMICROBIAL CHEMOTHERAPEUTIC POTENTIATION USING SUBSTITUTED NUCLEOSIDE DERIVATIVES

[75] Inventor: Michael G. Goodman, Rancho Santa Fe, Calif.

[73] Assignee: Scripps Clinic and Research Foundation, La Jolla, Calif.

[21] Appl. No.: 798,629

[22] Filed: Nov. 15, 1985

Related U.S. Application Data

[63] Continuation of Ser. No. 546,679, Nov. 1, 1983, Pat. No. 4,643,992.

[51] Int. Cl.$^4$ .............................................. A61K 31/70
[52] U.S. Cl. .......................................... 514/45; 514/43
[58] Field of Search .................... 514/43, 45; 424/85, 424/114; 435/68, 240

[56] References Cited

U.S. PATENT DOCUMENTS 3,798,210  3/1974  Pfleiderer ............................ 536/24
4,414,204  11/1983  Tarcsay et al. ....................... 424/114
4,428,937  1/1984  Howarth .............................. 424/114

Primary Examiner—Blondel Hazel
Attorney, Agent, or Firm—Dressler, Goldsmith, Shore, Sutker & Milnamow, Ltd.

[57] ABSTRACT

An antimicrobial composition and its method of use are disclosed. The composition contains an in vivo effective amount of an antibiotic and a potentiating amount of an immune response-enhancing agent. The immune response-enhancing agent corresponds in structure to a formula selected from

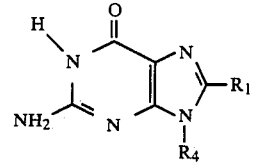

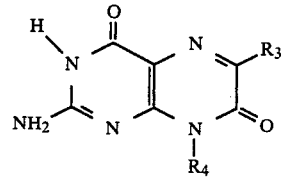

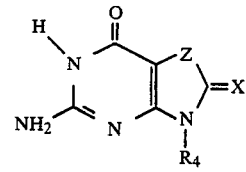

where X is O or S; Z is N—$R_2$, O or S; $R_1$, $R_2$ and $R_3$ are substituted groups; and $R_4$ is an aldoglycosidyl radical.

38 Claims, No Drawings

ANTIMICROBIAL CHEMOTHERAPEUTIC POTENTIATION USING SUBSTITUTED NUCLEOSIDE DERIVATIVES

CROSS-REFERENCE TO COPENDING APPLICATION

This is a continuation-in-part of copending application, Ser. No. 546,679, filed Nov. 1, 1983 now U.S. Pat. No. 4,643,992.

DESCRIPTION

1. Technical Field

The present invention relates to an antimicrobial composition and its method of use, and more particularly to a composition containing an effective amount of an antibiotic and a potentiating amount of an immune response-enhancing agent whose combined use aids in alleviating a microbial infection to a greater extent than the separate use of either ingredient.

2. Background Art

Upon successful infection of an animal host, microbial agents such as gram negative and gram positive bacteria, fungi and viruses grow and in so doing can cause injury to the host. Some microbes are beneficial such as the symbiotic *Escherichia coli* that live in the gut of most mammals and assist in the digestion of foods. Infection by pathogenic microbes, by definition, causes an infection that is injurious to the host.

Infection by pathogenic microbes initiates a number of responses in the host animal such as a mammal. In most instances, the pathogen is recognized as foreign by the host mammal's immune system, thereby activating the humoral and/or cellular immune response of the host. As a consequence, antibody-producing leucocytes are stimulated to produce and secrete antibodies to combat the infecting organism. The complement system can also be activated to combat the infecting organism, as can cells such as macrophages and neutrophils.

In many instances, the host's disease-fighting immune system cannot respond in time for the pathogenic microbe to be eliminated before the host dies. In certain cases the immune response is unable to eliminate the pathogen, and a state of chronic infection ensues. In other instances, as in AIDS, after receipt of immunosuppressive medication, or after radiation treatment where the immune system is suppressed, and also in cases such as hypogammaglobulinemia where the host is immunodeficient, the host often dies from an opportunistic infection. In such situations, exogenously supplied antimicrobial agents, antibiotics, are utilized to kill or slow the advance of the growing microbe while the immune system continues in its lower acting manner.

The use of anti-microbial drugs is not a panecea, however. Many pathogens have developed a tolerance or resistance to some commonly used drugs such as penicillin and tetracycline. Widespread and overuse of such drugs in animal feeds has been linked to an increase in the number and varieties of microbes that are no longer susceptible to such drugs.

Still further, and possibly more importantly, use of effective dosages of anti-microbial drugs also can cause toxicity problems for the host. Thus, the very materials that are toxic or static for the pathogens can also be toxic to the host they are used to treat.

For example, use of aminoglycoside antibiotics such as streptomycin and kanamycin are well known to lead to neurotoxicity and nephrotoxicity to varying degrees. A significant percentage of the human population is well known to shown hypersensitivity to penicillin, particularly after topical administration. Tetracyclines used in large doses have produced liver damage and are not used in children due to detrimental effects on growth of bones and teeth, while chloramphenicol can produce blood dyscrasias such as aplastic anemia. Polypeptide antibiotics such as bacitracin, the polymyxins and colistin are all nephrotoxic when administered systemically in large doses. Similarly, antifungal antibiotics such as nystatin and amphotericin B, which are also sometimes referred to as polyene antibiotics, can cause hemolytic anemia.

It would therefore be advantageous if the beneficial activity of an antibiotic could be used with less danger from that material's deleterious side effects. One manner of accomplishing that desired result is to use a potentiating agent that acts synergistically with the antibiotic so that less of the antibiotic can be used as an effective dose. To that end, Davis, B. D. et al., *Microbiology*, Harper & Row, Hoeber Medical Division, New York (1969) at page 641 wrote:

> "Some means of enhancing nonspecific immunity would obviously be of great value. To be effective, it would have to stimulate some general factor of antibacterial resistance, such as phagocytosis. Although no practical means of achieving this end is known, studies on bacterial endotoxins have revealed that in appropriate doses they enhance the phagocytic capabilities of leucocytes."

However, Parant et al., *Infect. Immun.*, 13: 722–727 (1976) reported a failure of andotoxin to increase nonspecific resistance to infection of lipopolysaccharide in low-responder mice (C3H/He).

Co-assigned U.S. Pat. No. 4,539,205 to Goodman and Weigle describes modulation of animal cellular responses with 8-substituted guanine derivatives bonded 9-1' to an aldose having 5 or 6 carbon atoms in the aldose chain (ring). The cellular modulations described in that patent relate mostly to immunomodulation such as adjuvanticity in producing primary and secondary immune responses. Activity against certain neoplastic conditions is also disclosed as are T cell-replacing activity, an IL-1 like activity on thymocytes, and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, while electron donating substituents such as an amino group were found to be inactive.

In addition, co-assigned, co-pending U.S. patent application Ser. No. 546,679 and its corresponding published European patent application No. 83306791.1 further discloses the use of derivatives of 8-hydroxyguanine (8-oxoguanine), 7-methyl-8-oxoguanine and 7-methyl-8-thioxo-guanine in modulating animal cellular responses. Further results using guanine derivatives disclosed in U.S. Pat. No. 4,539,205 are also disclosed as are similar results using guanine derivatives disclosed for the first time in that application.

U.S. Pat. No. 3,798,210 to Pfleiderer describes the synthesis of 8-(1'-glycosidyl)pteridines, including isoxanthopterin derivatives. That patent teaches the use of its compounds as the active pharmaceutical agents against specific pathogens such as malaria and tubercle bacilli, pathogenic fungi, gram-positive and gram-negative bacteria, and primarily against viruses such as herpes virus and influenza virus. Some of the compounds of the Pfleiderer patent are also useful herein, but not as antibiotics as is taught in Pfleiderer. This use is described hereinafter.

BRIEF SUMMARY OF THE INVENTION

The present invention contemplates an antimicrobial composition and a method of treating disease by administration of such a composition to a host animal, particularly a mammal.

The antimicrobial composition comprises a diluent amount of a physiologically tolerable carrier admixed with an in vivo effective amount of an antibiotic and a potentiating amount of an immune response-enhancing agent. The immune response-enhancing agent has a structure that conforms to a formula selected from the group consisting of

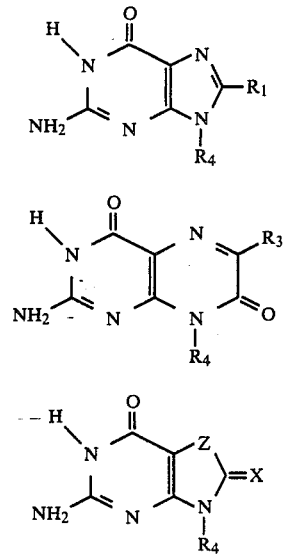

wherein

Z is O, S or N—$R_2$;

$R_1$ contains fewer than about 20 atoms and has a Hammett substituent sigma constant for ionization of a meta-substituted benzoic acid that is greater than that of hydrogen;

$R_2$ is a radical selected from the group consisting of lower alkyl, lower beta-alkenyl, benzyl, hydroxy lower alkyl, polyhydroxy lower alkyl, lower alkylene lower alkylcarboxylate, lower alkanoyl, lower alkylcarboxy, lower alkoxy lower alkyl carbonyl, and lower alkyl carboxamido in which the carboxamido group has the formula $CONR_9R_{10}$ wherein $R_9$ and $R_{10}$ are the same or different and are selected from the group consisting of hydrogen and lower alkyl or $NR_9R_{10}$ together form a heterocyclic ring having five or six atoms in the ring;

X is oxygen or sulfur;

$R_3$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo (O=), lower alkoxy, phenyl-lower alkoxy, halo, mercapto, thioxo (S=), lower alkylthio, phenyl-lower alkylthio, lower alkanoyl (lower acyl), carboxy, lower alkoxy carbonyl, lower alkylcarboxy, lower alkylene lower alkylcarboxylate, lower alkoxy lower alkyl carbonyl, and lower alkyl carboxamido in which the carboxamido group has the formula $CONR_9R_{10}$ wherein $R_9$ and $R_{10}$ are the same or different and are selected from the group consisting of hydrogen and lower alkyl or $NR_9R_{10}$ together form a heterocyclic ring having five or six atoms in the ring;

$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-subsituted lower alkyl, lower alkanoyl, benzyl and benzoyl derivatives wherein an O-substituent, if present on one oxygen, is present on all available ring substitutent oxygens;

the pharmaceutically acceptable salts of said agent; and the tautomers thereof.

The method of this invention contemplates treatment of a microbial infection in a mammalian host. Here, a before-described antimicrobial composition is administered to the host in a unit dose. A plurality of such doses can be administered over a time period of about one month in another embodiment. Still another embodiment contemplates that a first administration of the antimicrobial composition can be followed by a further plurality of administrations of unit doses of an effective amount of the antibiotic in a second composition, the further administrations occurring within a time period of about one month.

In yet another embodiment, an effective unit dose of the antibiotic and a potentiating unit dose of the immune response-enhancing agent are administered to the host separately, but in the presence of each other in vivo. Thus, whether administered together or separately, the antibiotic and immune response-enhancing agent are present together in vivo.

The present invention provides several benefits and advantages.

One benefit of the present invention is that a similar treatment response in overcoming the treated disease can be obtained using a smaller overall dosage of antibiotic than was previously possible.

Another benefit is that the incidence of antibiotic-induced toxicity can be reduced.

One advantage of this invention is that an immunosuppressed or immunodeficient host can be assisted in mounting an enhanced immune response to an opportunistic disease while the disease-causing microbe is also attacked chemotherapeutically. The enhanced immune response can be specific and/or nonspecific as to the infecting microbe.

Still another advantage of the instant invention is that the administration can be by peroral or perenteral routes.

Still further benefits and advantages will be apparent to those skilled in the art from the detailed description that follows.

DETAILED DESCRIPTION OF THE INVENTION

The present invention contemplates an antimicrobial composition and a method of its use. The composition comprises two active ingredients. One of those ingredients is an in vivo effective amount of an antibiotic, while the second is an immune response-enhancing agent, which when present in its own effective amount potentiates the antibiotic through stimulation of the immune system of the host mammal to which it is administered. It is thus found that although the two active ingredients act by different mechanisms on different entities; i.e., on the invading microbe and on the host's immune system, the action of the two ingredients is synergistic in providing an antimicrobial result superior to the result expected from either ingredient alone.

It is believed that the present invention is the first example of a combined, synergistic use of an antibiotic and an immune response-enhancing agent. Thus, while immunologically active ingredients such as an immunogen and an adjuvant have been combined, and two or more antibiotics have been combined, e.g., the 5:1 (w/w) mixtures of sulfadiazine and trimethoprim or sulfamethoxazole and trimethoprim, as well as the combined use of trisulfapyrimidines and pyrimethamine, there is no known prior attempt to combine an antibiotic and immune response-enhancing agent.

A. Antibiotics

The antibiotics useful herein are antimicrobial chemotherapeutic agents such as those well known in the art, and can be present in their usually used unit dosage amounts, which are also well known. Preferably, however, the effective amount is less than that usually used to treat a microbially-induced disease state.

Exemplary antibiotics include without limitation individual pharmaceuticals selected from the group consisting of beta-lactam, sulfonamide, aminoglycoside, polypeptide, tetracycline and polyene antibiotics. Antibiotics that are not as readily classified are also contemplated. Specific exemplary antibiotics are listed below, along with illustrative reported human unit dosages in parentheses.

Exemplary beta-lactams include the penicillins and cephalosporins such as penicillin G (0.6–12 million units), penicillin V potassium (125–500 mg q 6–8h), phenethicillin potassium (125–250 mg q 4–8h), carbenicillin (5 g q4h), methicillin (1–2 g q6h), oxacillin (0.5–1 g q4–6h), dicloxacillin sodium (0.125–0.5 g q6h), nafcillin (0.25–1 g q6h), ampicillin (0.25–0.5 g q6h), hetacillin (225–450 mg q6h), ticarcillin (50–300 mg q3–6h), cephalothin sodium (0.5–1 g q4–6h), cephaloridine (0.25–1g q8h), cephalexin (0.25–0.5 g q6h) and cefazolin sodium (0.25 g q8h–1 g q6h).

Exemplary sulfonamides include sulfadizine (4–6 g/day), sulfamerazine (4 g followed, by 1 g q6h), sulfisoxazole (2–4 g, followed by 4–8 g/day in 4–6 doses), sulfamethizole (250–500 mg q6h), sulfamethoxazole (400 mg q12h), sulfachloropyridazine (2–4 g, followed by 2–4 g/day in 3–6 divided doses), sulfamethoxypyridazine (1 g, followed by 500 mg/1–2 days), and sulfadimethoxine (1 g, followed by 500 mg/day).

Exemplary aminoglycoside antibiotics include streptomycin (0.5–2 g/day), neomycin sulfate (1 g q4h for 24–72 hours), kanamycin A (15 mg/kg/day divided q6h), gentamicin C (0.8–5 mg/kg/day divided q8h), tobramycin (3–5 mg/kg/day), amikacin (15 mg/kg/day) and spectinomycin (2–4 g).

Exemplary polypeptide antibiotics include bacitracin (10,000–20,000 units q 12–6h, not to exceed 100,000 units/day), polymyxin B sulfate (less than 4 mg/kg/day) and colistin sulfate (2–5 mg/kg/day).

Exemplary tetracycline antibiotics include tetracycline (0.25–5 g q6h), chlortetracycline (0.2–0.6 g/day), oxytetracycline (0.5–1 g q12h), demeclocycline (0.15–0.3 g q6h), minocycline (100 mg q 12h), doxycycline (0.1 g q12h on day 1, then 0.1 g/day) and methacycline (0.15 g q 6h).

Exemplary polyene antibiotics that are utilized against fungal infections include nystatin (500,000 units 3 times/day) and amphotericin B (0.25 mg/kg over 6 hours, increased to 1 mg/kg/administration/day). Other useful antifungal antibiotics are griseofulvin (500 mg/day) and flucytosine (12.5–37.5 mg/kg q6h).

Sulfones useful in treating leprosy include dapsone (50–100 mg/day), and sulfoxone (330 mg twice/week for 2 weeks, then 4 times/week for 2 weeks, daily 6 days/week thereafter).

Antibiotics that are not readily classified by family but are nevertheless useful include nalidixic acid (1 g q4h), chloramphenicol (12.5–25 mg/kg q6h), erythromycin (0.5 g q6h), vancomycin (1 g q12h), novobiocin sodium (500 mg q12h), lincomycin (0.5 g q6–8h), and clindamycin (0.15–0.45 mg q6h). Also in this group are the antiviral antibiotics such as iodoxuridine (430 mg/kg total over 5 days), amantadine (100 mg q12h), acyclovir (15 mg/kg/day), ketoconazole (200–400 mg/day), miconazole (200–1200 mg q8h) and human interferon. Drugs used in treating tuberculosis include isoniazid (3–5 mg/kg/day), streptomycin (before), ethambutol (25 mg/kg/day) and rifampin (600 mg/day as a single dose). Anti-malarial drugs include chloroquine (1 g, 0.5 g 6 hours later and daily for 2 days), amodiaquin (1.8 g in divided doses on day 1, followed by 0.6 g/day for 2–3 days), primaquine phosphate (26.3 mg/day for 14 days; to destroy exoerythrocytic malarial parasites), pyrimethamine (25–50 mg q1–2/week), quinine (1 g q8h).

Further information such as treatment regimens, structures, toxicity, and the like about the before-mentioned antibiotics can be found in *The Pharmaceutical Basis of Therapeutics*, Goodman and Gilman eds, 6th ed., The Macmillan Co., New York, NY (1980), and in Goth, A., *Medical Pharmacology*, 9th ed., The C. V. Mosby Co., St. Louis, MO, (1978), and in the citations therein. Specific, further information concerning many of the above antibiotics can also be found in the *Physicians' Desk Reference*, 27–39th editions, Medical Economics Company, Oradell, NJ, (1973–1985). Still further information concerning useful antibiotics can be found in *Remington's Pharmaceutical Sciences*, Osol ed., 16th ed., Mack Publishing Co., Easton, PA (1980), as well as in *Textbook of Organic Medicinal and Pharmaceutical Chemistry*, Wilson, Gisvold and Doerge eds., 7th. ed., J. B. Lippincott Co., Philadelphia, PA (1977). Appendix D of the latter volume provides a table of correspondence between the official titles (generic names) used herein, CAS Index names, IUPAC name, CAS registry numbers, empirical formulas, and molecular weights of the antibiotics disclosed herein.

B. Immune Response-Enhancing Agents

The immune response-enhancing agents are members of one of two classes of aldoglycosides, the (1) 8-substituted- and 7,8-disubstituted-9-aldoglycosidyl-guanines, and (2) the 6-substituted-8-aldoglycosidyl-isoxanthopterins. These compounds correspond generally in structure to formulas I and II, respectively hereinbelow,

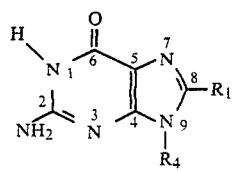

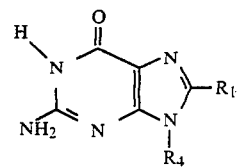

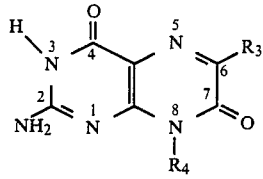

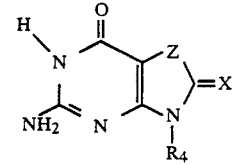

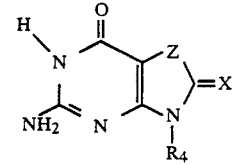

wherein R₁ and R₃ are 8- and 6-substituents, respectively, and R₄ is the aldoglycoside, all of which are discussed in detail hereinafter.

When $R_1$ is hydroxy or mercapto, the compounds of the formula I can tautomerize to place the endocyclic double bond that was at the 7,8-position at a position exocyclic to the ring, and provide a further useful valance for substitution on the nitrogen at the 7-position. The tautomerized hydroxy and mercapto groups are referred to as oxo and thioxo, respectively. The oxo and thioxo guanine derivatives are thus viewed as species of the compounds of formula I, above.

Certain of such tautomerized 7-substituted-8-oxo- and 7-substituted-8-thioxoguanine derivatives are useful herein, as are similar 7-oxa- and 7-thia-analogs of 8-oxo- or 8-thioxo-derivatives of guanine that are believed to exist substantially only in the 8-oxo and 8-thioxo forms. The structures of these compounds correspond to formula III, below

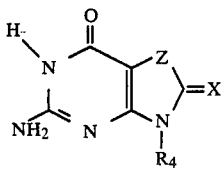

wherein Z is oxygen (O), sulfur (S) or substituted nitrogen (N—R₂); X is oxygen (O) or sulfur (S); R₂ is as described hereinafter; and R₄ is the aldoglycoside that is also described hereinafter. It is noted that the isoxanthopterin derivatives of formula II can also tautomerize when R₃ is hydroxy or mercapto, and form the corresponding oxo- and thioxosubstituted derivatives, respectively.

1. Guanine Derivatives

The guanine derivatives useful herein are readily prepared by procedures published in the chemical literature, or by procedures analogous thereto. Syntheses of 8-substituted guanine derivatives typically begin with the 9-1'-aldoglycoside bond already formed. The general mode of synthesis of such 9-(1'-beta-D-aldoglycosidyl)-guanines as are useful is known. Exemplary syntheses are illustrated in Holmes and Robins, *J. Am. Chem. Soc.*, 86, 1242–1243 (1964); Ibid., 87, 1772–1776 (1965); Long et al., *J. Org. Chem.*, 32, 2751–2756 (1967); Gerster et al., *J. Org. Chem.*, 33, 1070–1073 (1968), Rizkalla et al., *Biochim. Biophys. Acta*, 195, 285–293 (1969) and Miller et al., *Biochemistry*, 12, 5310–5319 (1973). Exemplary guanine derivatives have a structure that conforms to formulas I and III, below.

The R₁ group or radical of the compounds of formula I contains fewer than about 20 atoms, and more preferably, fewer than about 15 atoms. Most preferably, R₁ contains 1 to about 7 atoms. R₄ is the aldoglycosidyl radical that is discussed hereinafter.

One convenient way of characterizing useful R₁ groups (8-substituents) of the guanine derivative of formula I is by their electron withdrawing inductive effects relative to hydrogen. Hammett substituent sigma constants (sigma constants) calculated for ionization of meta-substituted benzoic acids are useful in predicting relative inductive effects, and are well known to those familiar with physical organic chemistry. See, for example, Hine, *Physical Organic Chemistry*, McGraw-Hill Book Company, New York, pp. 85–88 (1962).

Those substituents that have a greater inductive electron withdrawing effect than hydrogen have positive sigma constant values. Those substituents that exhibit less of an inductive electron withdrawing effect than hydrogen; i.e., electron donors, have negative sigma constant values.

Preferred R₁ groups have an inductive electron withdrawing effect greater than that of hydrogen. Illustrative of such 8-substituents are halo, hydroxy, mercapto, lower alkyloylthio (lower acylthio), lower alkyl sulfides also known as lower thioalkoxy radicals or lower alkylthio radicals, nitro, cyano, lower alkoxy, halomethyl such as bromomethyl or chloromethyl, carboxy, lower alkanoyl (lower acyl), trifluoromethyl, lower alkanamido (lower acylamido), lower alkyl sulfonyl, sulfonamide and methyleneoxy lower alkyl ethers such as methyleneoxyethyl (—CH₂—O—CH₂CH₃).

With reference to Hammett substituent sigma constants for meta benzoic acid substituents, the preferred 8-substituents have positive values. More preferably, the 8-substituents have sigma constants of about 0.1 to about 0.7. The most preferred 8-substituents have sigma constants of about 0.1 to about 0.4. It is noted that sigma constants have not been measured for all of the preferred 8-substituents. However, the absence of such a measurement for a 8-substituent is not an indication that the 8-substituent is not among the preferred class of substituents.

Where Z is N—R₂, the R₂ group of the guanine derivative of formula III is most preferably lower alkyl, lower beta-alkenyl and benzyl. Also contemplated are less preferred radicals that include hydroxy lower alkyl, lower alkanoyl, polyhydroxy lower alkyl, lower alkyl carboxy, lower alkoxy lower alkyl carbonyl, lower alkylene lower alkylcarboxylate, and lower alkyl carboxamido in which the carboxamido group has the formula CONR₉R₁₀ wherein R₉ and R₁₀ are the same or different and are selected from the group consisting of hydrogen and lower alkyl or NR$_9$R$_{10}$ together form a heterocyclic ring containing five or six atoms in the ring. It is particularly preferred that X be oxygen. A particularly preferred compound of formula III corresponds to the formula

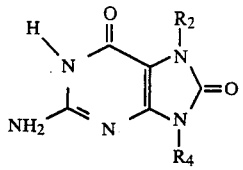

The guanine ring is itself free from electrically charged functionality other than carboxy, and that charge that is provided by hydrolysis reactions of water with the weakly basic amine substituents of the guanine ring. Thus, except where tautomerization can occur through an 8-hydroxy or 8-mercapto group, the nitrogen atom at the 7-position is unsubstituted since a substitution on that nitrogen would form a quaternary atom having a permanent positive charge. In addition, the useful guanine derivatives are free from phosphate groups that can bear an electric charge at physiological pH values.

2. Isoxanthopterin-8-Aldoglycosides

2-Amino-4-hydroxypteridine and its derivatives are known in the art as pterin and its derivatives, respectively. Prototropically active pterins are usually represented in their most favored tautomeric formula as 2-aminopterin-4-one and its derivatives, Pfleiderer, Chapter 2.16 in *Comprehensive Heterocyclic Chemistry*, Vol. 3, Part 2B, Katritzky and Rees eds., Pergamon Press, New York (1984) pages 63–327.

2-Amino-4,7-dihydroxypteridine and its tautomer 2-aminopterin-4,7-dione are known as isoxanthopterin. A more precise chemical name for isoxanthopterin is 2-amino-3,4,7,8-tetrahydro-4,7-dioxopteridine. The compounds useful herein will generally be referred to as isoxanthopterin and its derivatives. These useful isoxanthopterin derivatives all possess an aldoglycoside (sugar aldehyde) as a substituent at the 8-position of the pteridine ring system, and can also include a substituent other than hydrogen at the 6-position.

Isoxanthopterin and 6-substituted isoxanthopterins for preparation of the isoxanthopterin derivatives useful herein are themselves readily prepared by known reactions. In one reaction scheme, a 2,5,6-triamino-4-hydroxypyrimidine is reacted with an alpha-keto acid in which a substituent beta to the carboxy group forms the R$_3$ group in the structural formulas herein. See, Hurst, *An Introduction To The Chemistry And Biochemistry Of Pyrimidines, Purines And Pteridines*, John Wiley & Sons, New York, pages 86–103 (1980), and the citations therein. In another reaction scheme, the above pyrimidine is reacted with a di-lower alkyl ester of an acetylene dicarboxylic acid to form a lower alkyl carboxylic acid at the 6-position and lower alkyl esters thereof. Iwanami, *Bull. Chem. Soc. Japan*, 44: 1314 (1971). Still further compounds and reaction schemes are discussed in Pfleiderer, Chapter 2.16 of *Comprehensive Heterocyclic Chemistry*, supra.

The isoxanthopterin 8-aldoglycoside derivatives useful herein are preferably prepared from isoxanthopterin or a 6-substituted isoxanthopterin derivative to which the aldoglycosidic group is thereafter added by the method of Pfleider as described in U.S. Pat. No. 3,798,210, whose disclosures are incorporated herein by reference. Other methods of preparation such as the cyclization of a 2-amino-3,4-dihydro-5-nitro-4-oxo-6-aminoglysidyl-pyridmidine described by Lohrmann and Forrest, *J. Chem. Soc.*, 460–465 (1965) are also useful.

Briefly, in accordance with the Pfleider technique, a suitably substituted isoxanthopterin is O-metalized at the 7-position with a quadrivalent metal of the fourth main group and third to fifth period of the periodic system. The O-metalized compound so prepared is reacted with an aldoglycoside whose 1'-position hydroxyl group is itself derivatized as a reactive ester such as an ester of a lower carboxylic acid ester like acetic acid, or as an ether such as a lower alkyl ether like a methyl ether. The 1'-position hydroxyl can also be replaced by a halo group such as bromide as taught by Pfleider and his co-workers in *Chem. Ber.*, 106, 317–331 (1973); *Chem. Ber.*, 106, 1952–1975 (1973); and *Chem. Ber.*, 107, 339–361 (1974).

Quadrivalent germanium, tin and especially silicon are preferred O-metalizing agents. The particularly preferred O-metalizing agent is hexamethyldisilazane.

A strong acid catalyst such as an inorganic acid like sulfuric acid is preferably used with an O-metalizing agent such as hexamethyldisilazane. The hexamethyldisilazane is preferably utilized in excess, in the absence of water, and preferably in the presence of nitrogen or argon rather than air.

The 7-O-metalized isoxanthopterin is thereafter typically collected and reacted in an inert solvent such as dry benzene with the aldoglycoside whose hydroxyl groups other than that of the 1'-position are protected, as by benzoyl or acetyl groups. The 1'-position of the chosen aldoglycoside is derivatized as before discussed.

The glycosidation reaction is preferably carried out in the presence of a mercuric salt such as a mercuric halide, or mixture of mercuric halides where an aldoglycosidyl 1'-ether or 1'-ester is used. An elevated temperature such as that of refluxing benzene at one atmosphere of pressure is used for the aldoglycosylation reaction (condensation of sugar and isoxanthopterin).

The mercury salt, where used, is filtered from the reaction medium once the reaction is over, and the isoxanthopterin-8-(hydroxy protected-aldoglycoside) derivative is recovered as by column chromatography. The hydroxy protecting groups, e.g., benzoyl or acetyl, are thereafter removed by standard procedures such as reaction in sodium methoxidemethanol, followed by neutralization. The desired isoxanthopterin-8-(1'-aldoglycoside derivative is thereafter collected and purified, as by crystallization.

Useful isoxanthoperin derivatives have a structure that corresponds to formula II, before,

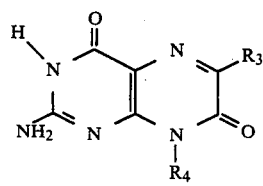

wherein
R$_3$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo (O=), lower alkoxy, phenyl-lower alkoxy, halo, mercapto, thioxo (S=), lower alkylthio, phenyl-lower alkylthio, carboxy, lower alkanoyl (lower acyl), lower alkoxy carbonyl, lower alkylcarboxy, lower alkylene lower alkylcarboxylate, lower alkoxy lower alkyl carbonyl, and lower alkyl carboxamido in which the carboxamido group has the formula $CONR_9R_{10}$ wherein $R_9$ and $R_{10}$ are the same or different and are selected from the group consisting of hydrogen and lower alkyl or $NR_9R_{10}$ together form a heterocyclic ring containing five or six atoms in the ring;

$R_4$ is an aldoglycoside radical as described hereinafter that is selected from the group consisting of 1'-aldopentosidyl, 1'-aldohexosidyl, mono-deoxygenated 1'-aldopentosidyl and mono-deoxygenated 1'-aldohexosidyl radicals bonded beta to the 8 position of an isoxanthopterin.

In particularly preferred practice, $R_3$ is hydrogen, hydroxy, lower alkyl, carboxy, lower alkoxy carbonyl, e.g., ethoxycarbonyl or methoxycarbonyl, and polyhydroxy lower alkyl.

Tautomers of the isoxanthopterin derivatives are also contemplated.

3. Exemplary $R_1$, $R_2$ and $R_3$ Radicals

Reference has been made hereinbefore to $R_1$, $R_2$ and $R_3$ groups and radicals of an immune response-enhancing agent. Examples of those previously mentioned groups and radicals are provided hereinbelow as those radicals are applicable to the compounds of formulas I, II and III discussed hereinbefore. Consequently, where a group or radical can be an $R_1$ and an $R_3$ group or radical, that moiety can have at most about 20 atoms as an $R_1$, while a greater number of atoms is allowed for an $R_3$ group or radical. Groups and radicals referred to as "lower" denote that they possess 1 to about 6 carbon atoms, and preferably 1 to about 3 carbon atoms.

Lower alkyl radicals include, for example, methyl, ethyl, propyl, iso-propyl, n-butyl, sec-butyl, t-butyl, n-pentyl, 2-methyl-3-butyl, 1-methylbutyl, 2-methylbutyl, neo-pentyl, n-hexyl, 1-methylpentyl, 3-methylpentyl, 1-ethylbutyl, 2-ethylbutyl, 2-hexyl, 3-hexyl, and the like.

Hydroxy lower alkyl radicals include hydroxy methyl, 2-hydroxyethyl, 2-hydroxypropyl, 3-hydroxypropyl, 3-hydroxy-2-butyl, 3-hydroxy-2,2-dimethylpropyl, 6-hydroxyhexyl and the like.

Polyhydroxy lower alkyl radicals include 1,2-dihydroxyethyl, 1,2,3-trihydroxypropyl, 2,3-dihydroxypropyl, 3,4-dihydroxybutyl and the like. Those skilled in the art will understand that the contemplated polyols contain no more than one hydroxyl group on each carbon atom of the lower alkyl group.

Phenyl-lower alkyl radicals include phenyl-substituted lower alkyl radicals listed above, wherein the alkyl portion of the radical is bonded to the 6-position of the isoxanthopterin derivative. Exemplary radicals include benzyl, phenethyl, 2-phenylpropyl, 2-phenyl-3-methylpentyl and the like.

Lower alkyl phenyl radicals are the above-described lower alkyl radicals substituted on a phenyl radical that is itself bonded to the 6-position of an isoxanthopterin 8-aldoglycoside. Exemplary of such lower alkyl phenyl radicals are o-xylyl, p-(2-hexyl)phenyl, m-(iso-propyl)-phenyl, and the like. Trifluoromethylphenyl substituted ortho, meta or para to the position of binding to the 6-position of the isoxanthopterin constitute a sub-class of lower alkyl phenyl radicals.

Lower alkoxy phenyl radicals are lower alkyl ethers of ortho-, meta- or para-isoxanthopterin substituted phenols, wherein the lower alkyl group is as described before. Exemplary lower alkoxy phenyl radicals include o-methoxyphenyl, m-sec-butoxyphenyl, and p-(2-ethylbutoxy)phenyl.

Halophenyl radicals utilize halogen-substituted phenyl radicals in which the halogen is preferably fluoro, chloro and bromo, and also include iodo. Exemplary radicals include o-chlorophenyl, p-fluorophenyl and m-bromophenyl.

Hydroxy and mercapto radicals can also be present as oxo and thioxo radicals, respectively, due to their tautomer formation, as already noted.

Lower alkoxy radicals can be viewed as ethers formed from an 8-hydroxy guanine or a 6-hydroxy isoxanthopterin and a before-described lower alkyl group. Exemplary radicals include methoxy, ethoxy, propoxy, iso-propoxy, n-butoxy, and the like. Phenyl-lower alkoxy radicals can similarly be viewed as ethers formed from a 6-hydroxy isoxanthopterin and a before-described phenyl-lower alkyl radical. Exemplary of these materials are benzyloxy, 2-phenylethoxy, 2-phenylpropoxy and the like.

Halo radicals preferably include chloro, bromo, as well as fluoro and iodo.

Lower alkylthio and phenyl-lower alkylthio radicals are sulfide ethers and are thus analogous to the oxygen ethers described above, as lower alkoxy and phenyl-lower alkoxy radicals, respectively.

A carboxy radical is a carboxylic acid ($-CO_2H$) bonded to the 8- or 6-position of the guanine derivative or isoxanthopterin 8-aldoglycoside, respectively. A lower alkoxy carbonyl radical can be viewed as an ester of a carboxy substituent formed with a lower alkyl alcohol where the lower alkyl portion of the alcohol is a lower alkyl radical as before-described. Exemplary esters are ethyl, methyl, t-butyl, neo-pentyl carboxylates, and the like. These esters can also be named ethoxycarbonyl, methoxycarbonyl, t-butoxycarbonyl and neo-pentoxycarbonyl, respectively.

Lower alkyl carboxy radicals are the before-described lower alkyl radicals that further include a carboxy group. Lower alkoxy lower alkyl carbonyl radicals can be viewed as esters of substitutent lower alkyl carboxy radicals with lower alkyl alcohols, which are as described immediately above. Exemplary lower alkyl carboxy radicals include carboxymethyl, 2-carboxyethyl, 2-carboxyhexyl and the like. Exemplary lower alkoxy lower alkyl carbonyl radicals include 3-isopropoxycarbonylpropyl, 4-hexyloxycarbonylpentyl, and the like.

Lower beta-alkenyl radicals, as can be the $R_2$ portions of the compounds of formula III, contain an ethylenic double bond beta to the 7-nitrogen atom of the compound of that formula. Exemplary radicals include allyl, 3-but-1-enyl, 2-pentenyl, 3-methyl-2-pentenyl and the like.

Mono- and disubstituted lower alkyl amides can be viewed as being formed from a substituent carboxy group and a mono-lower alkyl amine or di-lower alkyl amine, respectively, where the lower alkyl radicals are as before described. Exemplary of such amines are methylamine, propyl-amine, sec-butylamine, hexylamine, dimethylamine, methylethylamine, butylhexylamine and the like. Amides of cyclic secondary amines having five or six atoms in the ring can be viewed as being formed from a carboxy group and a secondary amine such as pyrrolidine, morpholine, piperidine, pyrrole and 4-methylpiperazine. Unsubstituted amides are formed from ammonia as the amine.

Lower alkylcarboxamido radicals can be viewed as being formed from a lower alkyl carboxy substituent and an amine. the carboxamido group has the formula $CONR_9R_{10}$ wherein $R_9$ and $R_{10}$ are the same or different and are selected from the group consisting of hydrogen and lower alkyl. Alternatively, $NR_9R_{10}$ together can form a heterocyclic ring having five or six atoms in the ring. Exemplary useful amines are as discussed above.

Lower alkanoyl radical substituents, also known as lower acyl radicals, contain a carbonyl group bonded directly to the 8-position of the guanine, the 6-position of the isoxanthopterin ring or the 7-position nitrogen atom of a guanine derivative of formula III in which $R_2$ is the lower alkanoyl radical, thereby making the compounds ketones, an aldehyde or an amide, as is appropriate. Exemplary lower alkanoyl groups include formyl, acetyl, propionyl, 2-methylpropionyl, butyryl, 3-methylvaleryl and the like. The acyl carbon of the radical is considered a part of the "lower" alkanoyl or acyl group.

A lower alkylene lower alkylcarboxylate radical can be viewed as an ester of a substituent hydroxy lower alkyl radical and a lower alkyl carboxylic acid. Exemplary hydroxy lower alkyl substituents have been discussed previously, as have the lower alkanoyl (lower acyl) portions of lower alkyl carboxylic acids that can be present in such esters.

Lower alkyloylthio or lower acylthio radicals can be viewed as thioesters formed from an appropriate 6- or 8-mercapto substituent of an isoxanthopterin or guanine derivative, respectively, and a lower alkyl carboxylic acid. Exemplary of such radicals are thioacetyl, thiopropionyl, thiohexanoyl and the like. A lower alkanamido (lower acylamide) radical is an amide that can be viewed as being formed from an 8-amino guanine derivative and a lower alkylcarboxylic acid. Examplary of such radicals are formamido, acetamide, valaramido and the like. Thus, 8-acylamido guanine derivatives are useful while the corresponding amines are not.

Lower alkyl sulfonyl radicals contain an $—SO_2—$ group (sulfone) bonded to the 8-position of a guanine derivative and also to a lower alkyl group, as described hereinbefore.

The guanines and isoxanthopterin 8-aldoglycosides are weak bases, and as such can form acid addition salts. Such salts are useful in providing storage stability and do not provide an added electric charge to a useful guanine derivative in situ because of the large buffering effect provided by the host's blood and lymph systems. Pharmaceutically acceptable, non-toxic acid addition salts of guanines and isoxanthopterin derivatives are useful herein, and can be formed by treatment of the immune response-enhancing agent with an appropriate acid. Exemplary inorganic acids include hydrochloric, hydrobromic, sulfuric, phosphoric and the like acids. Exemplary organic acids include acetic, propionic, glycolic, pyruvic, malonic, succinic, maleic, fumaric, malic, tartaric, citric, benzoic, cinnamic, mendelic, methanesulfonic, ethanesulfonic, benzenesulfonic, p-toluenesulfonic, salicylic, p-aminosalicylic and the like acids. Conversely, the acid addition salt form can be converted to the free base form by treatment with alkali.

Useful immune response-enhancing agents also include 8- or 6-substituted carboxylic acids and lower alkyl substituted carboxylic acids of guanine and isoxanthopterin derivatives, respectively, as already noted. Basic salts of those carboxylic acids are also contemplated, and are formed by treatment of the carboxylic acid with an appropriate alkaline reagent to form, for example, guanosine-8-carboxylate cation salt or 6-isoxanthopterin 8-aldoglycoside carboxylate cation salt. Exemplary non-toxic cation salts of such carboxylic acids include sodium, potassium, zinc, aluminum, calcium, magnesium, and the like.

4. Aldoglycosides

The aldoglycoside portion ($R_4$) of the useful guanine and isoxanthopterin derivatives are cyclic, contain 5 or 6 carbon atoms, and are selected from the group consisting of 1'-aldopentosidyl, 1'-aldohexosidyl, mono-deoxygenated 1'-aldopentosidyl, and mono-deoxygenated-1'-aldohexosidyl radicals. The useful aldoglycosides are bonded to the 9- or 8-postion of the guanine or isoxanthopterin derivative, respectively. The aldoglycosides are free from electric charge and are therefore free from carboxy, phosphate and quaternary ammonium substituents.

Exemplary 1'-aldopentosidyl radicals are the 1'-radicals of ribose, arabinose, lyxose and xylose that are named 1'-ribofuranosidyl, 1'-arabinofuranosidyl, 1'-lyxofuranosidyl, and 1'-xylofuranosidyl radicals, respectively. Exemplary 1'-aldohexosidyl radicals are the 1'-radicals of glucose, galactose, mannose, gulose, allose, altrose, and rhamnose that are named 1'-glucopyranosidyl, 1'-galactopyranosidyl, 1'-mannopyranosidyl 1'-gulopyranosidyl, 1'-allopyranosidyl, 1'-altropyranosidyl, 1'-rhamnopyranosidyl, radicals, respectively. An exemplary mono-deoxygenated 1'-aldopentosidyl radical is that of deoxyribose that is named the 1'-(2'-deoxy)-ribofuranosidyl radical. An exemplary mono-deoxygenated 1'-aldohexosidyl radical is that of deoxygulose, named the 1'-(2'-deoxy)gulopyranosidyl radical.

Useful aldoglycosidyl radicals can have one or more hydroxyl groups esterified by a lower alkanoyl radical such as formyl, acetyl, propionyl or hexanoyl, and also by a benzoyl radical. Aldoglycosidyl radicals are also useful when etherified by lower alkyl, especially methyl and ethyl radicals, while benzyl ethers are also useful.

Suitable aldoglycosidyl radicals conform to the formula

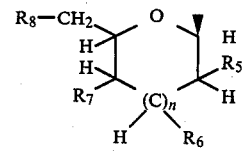

wherein
n is one or zero;
$R_5$ is hydrogen, hydroxy, lower alkoxy such as methoxy and ethoxy (and others as described before), benzyloxy, lower alkanoyloxy such as formyloxy, acetoxy (and other lower alkyl carboxylate radicals as are described before) or benzoxy.

$R_6$ when present, as well as $R_7$ and $R_8$ are all the same. These radicals can be hydroxy, a lower alkyl ether (lower alkoxy) such as methoxy and ethoxy, a benzyl ether (benzyloxy), a lower alkanoyl radical (lower acyl)

such as formyloxy, acetoxy, or a benzoate ester (benzoxy). When $R_5$ is other than hydrogen, $R_5=R_6$ when present$=R_7=R_8$. Thus, an O-substituent, when present on one oxygen is present on all available ring substituent oxygens.

The bonds of the above formula are not intended to convey any particular stereo specific configuration, except at the 1'-position at which the beta anomer is indicated.

In preferred practice, the aldoglycosidyl radical is selected from the group consisting of 1'-ribofuranosidyl, 1'-glucopyranosidyl, and 1'-(2'-deoxy)ribofuranosidyl radicals. Thus, preferably, when n is zero and $R_5$, $R_7$ and $R_8$ are all hydroxy, $R_6$ is absent, the aldoglycosidyl radical is selected from the group consisting of 1'-ribofuranosidyl; when n is zero, $R_5$ is hydrogen and $R_7$ and $R_8$ are hydroxy, $R_6$ is absent, the aldoglycosidyl radical is 2'-deoxy-1'-ribofuranosidyl; and when n is 1, and $R_5=R_6=R_7=R_8=$hydroxy, 1'-glucopyranosidyl is the aldoglycosidyl radical.

As already noted, the aldoglycoside is bonded from its 1'-position to the 9-position of a guanine derivative and to the 8-position of isoxanthopterin. When named as a guanine derivative, that bonding can be described as a 9-1'bond, while when named as an isoxanthopterin derivative, that bonding can be described as an 8-1'bond. The beta anomer of the aldoglycoside is that preferred herein, although mixtures of alpha and beta anomers are also useful. The aldoglycoside utilized is in the D stereo configuration and that configuration is implied where it is not stated.

5. Exemplary Immune Response-Enhancing Agents

Structural formulas of exemplary immune response-enhancing agents useful in a composition and method of this invention are shown below, wherein $R_1$, $R_2$, $R_3$ and $R_4$ are as shown in Table 1 following the structural formulas.

TABLE 1

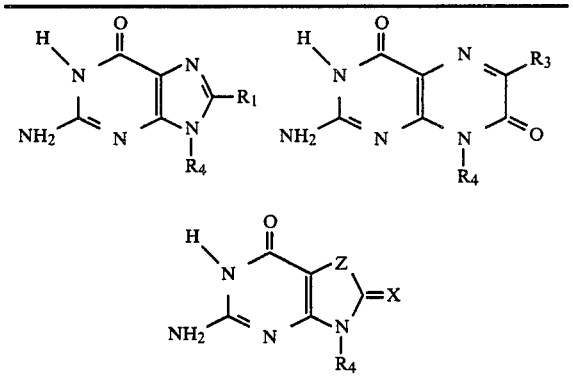

| R Group | | $R_4$ |
|---|---|---|
| $R_2$ | methyl, X = O | 1'-ribofuranosidyl |
| $R_3$ | iso-propyl | 1'-lyxofuranosidyl |
| $R_2$ | n-butyl, X = O | 1'-arabinofuranosidyl |
| $R_3$ | n-hexyl | 1'-gulopyranosidyl |
| $R_1$ | nitro | 1'-(2'-deoxy)ribofuranosidyl |
| $R_1$ | acetamido | 1'-xylofuranosidyl |
| $R_2$ | benzyl, X = O | 1'-allopyranosidyl |
| $R_3$ | phenethyl | 1'-mannopyranosidyl |
| $R_3$ | 2-phenylpropyl | 1'-(2',3',4',6'-tetra-O—acetyl)-glucopyranosidyl |
| $R_3$ | 2-phenyl-3-methylpentyl | 1'-(2',3',5'-tri-O—acetyl)-ribofuranosidyl |
| $R_3$ | o-xylyl | 1'-(2',3',5'-tri-O—acetyl)-arabinofuranosidyl |

TABLE 1-continued

| R Group | | $R_4$ |
|---|---|---|
| $R_3$ | p-(2-hexyl)phenyl | 1'-(2'-deoxy-3',5'-di-O—methyl)ribofuranosidyl |
| $R_3$ | N—methyl carboxamidomethyl | 1'-(2',3',4',6'-tetra-O—ethyl)glucopyranosidyl |
| $R_3$ | p-(trifluoromethyl)phenyl | 1'-(2',3',5'-tri-O—benzyl)-ribofuranosidyl |
| $R_3$ | o-methoxypheyl | 1-(2',3',5'-tri-O—benzoyl)-ribofuranosidyl |
| $R_3$ | ethylenepropionate | 1'-(2',3',4',6'-tetra-O—ethyl)glucopyranosidyl |
| $R_3$ | p-(2-ethylbutoxy)-phenyl | 1'(2'-deoxy-3',5'-di-O—methyl)ribofuranosidyl |
| $R_3$ | o-chlorophenyl | 1'-gulopyranosidyl |
| $R_3$ | m-bromophenyl | 1'-allopyranosidyl |
| $R_3$ | p-fluorophenyl | 1'-altropyranosidyl |
| $R_1$ | hydroxy | 1'-ribofuranosidyl |
| $R_1$ | mercapto | 1'-ribofuranosidyl |
| $R_1$ | methoxy | 1'-ribofuranosidyl |
| $R_1$ | iso-propoxy | 1'-xylofuranosidyl |
| $R_1$ | n-hexyloxy | 1'-(2'-deoxy)ribofuranosidyl |
| $R_1$ | benzoxy | 1'-ribofuranosidyl |
| $R_3$ | 2-phenylethoxy | 1'-lyxofuranosidyl |
| $R_3$ | 2-phenylpropoxy | 1'-(2'-deoxy)gulopyranosidyl |
| $R_1$ | chloro | 1'-ribofuranosidyl |
| $R_3$ | chloro | 1'-glucopyranosidyl |
| $R_1$ | bromo | 1'-(2'-deoxy)ribofuranosidyl |
| $R_3$ | fluoro | 1'-ribofuranosidyl |
| $R_1$ | iodo | 1'-ribofuranosidyl |
| $R_1$ | methylsulfido | 1'-ribofuranosidyl |
| $R_1$ | benzylsulfido | 1'-arabinofuranosidyl |
| $R_2$ | carboxy, X = O | 1'-lyxofuranosidyl |
| $R_3$ | carbomethoxy | 1'-ribofuranosidyl |
| $R_3$ | carbethoxy | 1'-(2'-deoxy)ribofuranosidyl |
| $R_3$ | carbo-t-butoxy | 1'-xylofuranosidyl |
| $R_1$ | carbo-neo-pentoxy | 1'-glucopyranosidyl |
| $R_2$ | methylcarboxy, X = S | 1'-gulopyranosidyl |
| $R_3$ | n-butylcarboxy | 1'-mannopyranosidyl |
| $R_2$ | ethylcarbomethoxy, X = O | 1'-(2',3',4',6'-tetra-O—acetyl)glucopyranosidyl |
| $R_3$ | sec-butyl-carbohexyloxy | 1'-(2',3',5'-tri-O—acetyl)-ribofuranosidyl |
| $R_3$ | sodium carboxy | 1'-(2',3',5'-tri-O—acetyl)-arabinofuranosidyl |
| $R_3$ | hydroxymethyl | 1'-(2',3',5'-tri-O—methyl)-ribofuranosidyl |
| $R_2$ | allyl, X = O | 1'-(2',3',4',6'-tetra-O—benzyl)allopyranosidyl |
| $R_3$ | 1,2-dihydroxyethyl | 1'-(2'-deoxy)ribofuranosidyl |
| $R_3$ | 1,2,3-trihydroxy-propyl | 1'-rhamnopyranosidyl |
| $R_2$ | 2-hydroxyethyl, X = O | 1'-ribofuranosidyl |
| $R_2$ | 2-carboxyethyl, X = S | 1'-arabinofuranosidyl |
| $R_2$ | 2-(N,N—dimethyl)-carboxamido, X = O | 1'-(2'-deoxy)gulo-pyranosidyl |

TABLE 1-continued

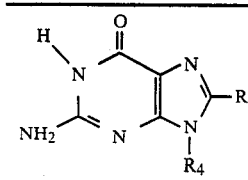

| R Group | | R4 |
|---|---|---|
| R2 | 1-methyl-2-(N—morphylinyl)-carboxamido, X = O | 1'-lyxofuranosidyl |

Structural formulas of further examples of immune response-enhancing agents useful in a composition and method of this invention are shown below, wherein Z, X and R4 are shown in Table 2 following the structural formula.

TABLE 2

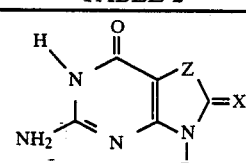

| Z | X | R4 |
|---|---|---|
| O | O | 1'-ribofuranosidyl |
| O | O | 1'-lyxofuranosidyl |
| O | O | 1'-glucopyranosidyl |
| O | O | 1'-(2'-deoxy)ribofuranosidyl |
| S | O | 1'-gulopyranosidyl |
| S | O | 1'-allopyranosidyl |
| S | O | 1'-xylofuranosidyl |
| S | O | 1'-(2',3',4',6'-tetra-O—methyl)gulopyranosidyl |
| S | S | 1'-ribofuranosidyl |
| S | S | 1'-allopyranosidyl |
| S | S | 1'-(2',3',5'-tri-O—benzoyl)-galactopyranosidyl |
| O | S | 1'-mannopyranosidyl |
| O | S | 1'-ribofuranosidyl |
| O | S | 1'-(2',3',4',6'-tetra-O—benzyl)altropyranosidyl |

Particularly preferred 8-substituted guanine derivatives have $R_1$ groups selected from the group consisting of halo, hydroxy, mercapto, lower alkylthio, and lower alkoxy radicals at the 8-position.

For the tautomeric 7-substituted-8-oxo- and 8-thioxoguanine derivatives, the 8-substituent is preferably oxo, and the particularly preferred 7-substituents are lower alkyl, lower beta-alkenyl and benzyl radicals. The 8-substituent of 7-oxa- and 7-thiaguanine derivatives is also preferably oxo, while a 7-oxaguanine derivative is preferred over a 7-thiaguanine derivative.

Particularly preferred isoxanthopterin 8-aldoglycosides are those having an $R_3$ group selected from the group consisting of hydrogen, hydroxy, lower alkyl, carboxy, lower alkoxy carbonyl, and polyhydroxy lower alkyl bonded at the 6-position.

For each of the immune response-enhancing agents, the 9-1'-aldoglycoside or the 8-1'-aldoglycoside portions, as appropriate, of the molecule are preferably beta-1-ribofuranosidyl, beta-1'-(2'-deoxy)ribofuranosidyl, or beta-1'-glucopyranosidyl. Exemplary of such particularly preferred materials are:

8-(1'-beta-D-ribofuranosidyl)isoxanthopterin;
8-(1'-beta-D-2'-deoxyribofuranosidyl)isoxanthopterin;
8-(1'-beta-D-glucopyranosidyl)isoxanthopterin; 6-hydroxy-8-(1'-beta-D-ribofuranosidyl)isoxanthopterin; 6-hydroxy-8-(1'-beta-D-2'-deoxyribofuranosidyl)isoxanthopterin; 6-hydroxy-8-(1'-beta-D-glucopyranosidyl)isoxanthopterin; 6-methyl-8-(1'-beta-D-ribofuranosidyl)isoxanthopterin; 6-methyl-8-(1'-beta-D-glucopyranosidyl)isoxanthopterin; 6-methyl-8-(1'-beta-D-2'-deoxyribofuranosidyl)isoxanthopterin; 6-carboxy-8-(1'-beta-D-ribofuranosidyl)isoxanthopterin; 6-carboxy-8-(1'-beta-D-glucopyranosidyl)isoxanthopterin; 6-carboxy-8-(1'-beta-D-2'-deoxyribofuranosidyl)isoxanthopterin; 6-methoxycarbonyl-8-(1'-beta-D-ribofuranosidyl)isoxanthopterin; 6-methoxycarbonyl-8-(1'-beta-D-2'-deoxyribofuranosidyl)isoxanthopterin; 6-methoxycarbonyl-8-(1'-beta-D-glucopyranosidyl)isoxanthopterin; 6-hydroxycarbonyl-8-(1'-beta-D-2'-deoxyribofuranosidyl)isoxanthopterin; 6-hydroxy-8-(1'-beta-D-ribofuranosidyl)isoxanthopterin 6-hydroxycarbonyl-8-(1'-beta-D-glucopyranosidyl)isoxanthopterin; 6-methoxy-8-(1'-beta-D-2'-deoxyfuransidyl)isoxanthopterin; 8-mercaptoguanosine (8-thioxoguanosien or 8-mercapto-9-(1'-beta-D-ribofuranosidyl)guanine; 8-mercapto-9-(1'-beta-D-2'-deoxyribofuranosidyl)guanine; 8-mercapto-9-(1'-beta-D-glucopyranosidyl)guanine; 8-hydroxyguanosine (8-oxoguanosine) or 8-hydroxy-9-(1'-beta-D-ribofuranosidyl)guanine; 8-hydroxy-9-(1'-beta-D-2'-deoxyribofuranosidyl)guanine; 8-hydroxy-9-(1'-beta-D-glucopyranosidyl)guanine; 7-methyl-8-oxoguanosine or 7-methyl-8-oxo-9-(1'-beta-D-ribofuranosidyl)guanine; 7-methyl-8-oxo-9-(1'-beta-D-2'-deoxyribofuranosidyl)guanine; 7-methyl-8-oxo-9-(1'-beta-D-glucopyranosidyl)guanine; 7-allyl-8-oxoguanosine or 7-allyl-8-oxo-9-(1'-beta-D-ribofuranosidyl)guanine; 7-allyl-8-oxo-9-(1'-beta-D-2'-deoxyribofuranosidyl)guanine; 7-allyl-8-oxo-9-(1'-beta-D-glucopyranosidyl)guanine; 7-benzyl-8-oxoguanosine or 7-benzyl-8-oxo-9-(1'-beta-D-ribofuranosidyl)guanine; 7-benzyl-8-oxo-9-(1'-beta-D-2'-deoxyribofuranosidyl)guanine; 7-benzyl-8-oxo-9-(1'-beta-D-glucopyranosidyl)guanine; 8-bromoguanosine or 8-bromo-9-(1'-beta-D-ribofuranosidyl)guanine; 8-bromo-9-(1'-beta-D-2'-deoxyribofuranosidyl)guanine; 8-bromo-9-1'-beta-D-glucopyranosidyl)guaine; 8-chloroguanosine or 8-chloro-9-(1'-beta-D-ribofuranosidyl)guanine; 8-chloro-9-(1'-beta-D-2'-deoxyribofuranosidyl)guanine; 8-chloro-9-1'-beta-D-glucopyranosidyl)quanine; 8-methylthioguanosine or 8-methylthio-9-(1'-beta-D-ribofuranosidyl)guanine; 8-methylthio-9-(1'-beta-D-2'-deoxyribofuranosidyl)guanine; 8-methylthio-9-(1'-beta-D-glucopyranosidyl)guanine; 7-oxa-8-oxoguanosine or 7-oxa-8-oxo-9-(1'-beta-D-ribofuranosidyl)guanine; 7-oxa-8-oxo-9-(1'-beta-D-2'-deoxyribofuranosidyl)guanine; and 7-oxa-8-oxo-9-(1'-beta-D-glucopyranosidyl)guanine.

Most preferred immune response-enhancing agents useful herein are those compounds in which R4 is the 1'-beta-D-ribofuranosidyl radical, in which $R_1$, $R_2$ and $R_3$ are particularly preferred, X is oxygen, and Z is N—$R_2$, as discussed before. These most preferred compounds have structures that conform to the formulas:

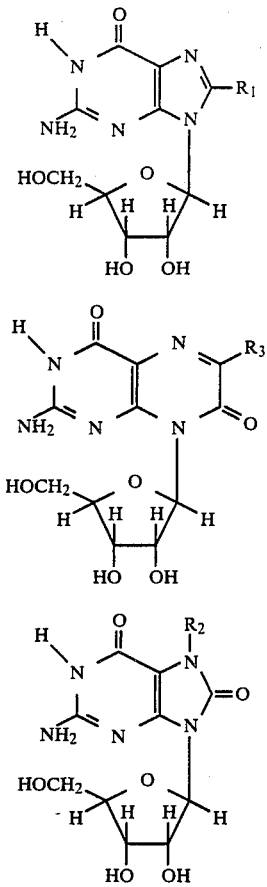

C. Compositions and Their Administration

The compositions of this invention comprise an in vivo effective amount of an antibiotic and a potentiating amount of an immune response-enhancing agent as the active ingredients. Those ingredients are admixed with a physiologically tolerably carrier. The composition can be administered perorally or parenterally to the host mammal in customary unit dosages; i.e., as a composition in unit dosage form comprising a physiologicaly tolerable carrier admixed with an effective amount of antibiotic and a potentiating amount of immune response-enhancing agent.

The term "unit dosage" and its grammatical equivalents as used herein refer to physically discrete units suitable as unitary dosages for human patients and other warm blooded animals, each unit containing a predetermined effective and potentiating amount of the two active ingredients calculated to produce the desired therapeutic effect in association with the required physiologically tolerable carrier, e.g. a diluent or a vehicle. The specifications for the novel unit dosage forms of this invention are dictated by and are directly dependent on (a) the unique characteristics of the active ingredients and the particular therapeutic effect to be achieved, and (b) the limitations inherent in the art of compounding such an active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions, emulsions and suspensions.

The amount of active ingredients that are administered in vivo depends on the age and weight of the patient, the particular condition to be treated and its severity, the frequency of administration, and the route of administration.

Illustrative in vivo effective amounts of exemplary antibiotics have already been provided. It is noted, however, that an antibiotic useful herein need not be administered in its usually used in vivo effective amount. Rather, in one aspect of this invention, less than a usually used in vivo amount of an antibiotic is utilized but is effective in alleviating the infection because of the potentiation provided by the immune response-enhancing agent. Such a less-than-usual amount can be determined by comparisons based on usually used laboratory techniques.

The potentiating dose range for a guanine derivative (formulas I and III) is about 1 to about 1000 milligrams per kilogram of body weight (1–1000 mg/kg), while that of an isoxanthopterin derivative is about 0.01 to about 200 mg/kg. More preferably, a guanine derivative is administered at about 5 to about 250 mg/kg, while an isoxanthopterin is administered at about 0.1 to about 25 mg/kg. Most preferably, a guanine derivative is present at about 10 to about 100 mg/kg, while an isoxanthopterin is present at about 1 to about 10 mg/kg.

A human adult dose of an immune response-enhancing agent is in the range of about 50 to about 50,000 mg/day for a guanine derivative, and about 5 to about 1400 mg/day for an isoxanthopterin derivative, given either as a single dose or in 2 to about 6 divided doses that are given at about 12 to 2 hour intervals. Veterinary dosages generally correspond to human dosages with the amounts administered being in proportion to the weight and metabolic rate of the animal as compared to adult humans.

A composition can be a solid or a liquid. The two active ingredients can be admixed as a suspension of solids in a solid or liquid physiologically tolerable carrier, or dissolved as a solute or suspended in the carrier, or a combination thereof.

Physiologically tolerable carriers are well known in the art. Exemplary of liquid carriers are sterile aqueous solutions that can contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. These latter carriers are exemplified by Ringer's Injection, Dextrose Injection, Dextrose and sodium chloride Injection and Lactated Ringer's Injection.

Liquid compositions can also contain liquid phases in addition to and to the exclusion of water. Exemplary of such additional liquid phases are glycerin, vegetable oils such as cottonseed oil, and water-oil emulsions.

Exemplary solid carriers include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Additionally, the solid carrier can include biodegradable and nonbiodegradable polymers, polypeptide carriers, affinity carriers such as AFFI-GEL 601 (phenyl boronate resin available from Bio-Rad Laboratories, Richmond, CA), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide methyl ester sweetener sold under the trademark NUTRASWEET (aspartame) by G. D. Searle Co.

An antimicrobial composition useful herein is administered to a mammalian host perorally or parenterally, as noted before. A composition of this invention can be administered once during a treatment regimen, such as a one month time period, or more preferably a one to about two week period of time. That administration is typically followed by a plurality of administrations of an in vivo effective amount of the antibiotic alone, or admixed with a physiologically tolerable carrier. Typically, an immune response-enhancing agent of this invention is administered less frequently during a treatment period than is the antibiotic without an immune response-enhancing agent, as dictated by the respective half-lives in vivo of the two active ingredients.

Where the in vivo effective amount of antibiotic (a) in an antimicrobial composition of this invention, and (b) in the following sole antibiotic administrations is the usually used dose of that drug for treating the pathogen, an improvement in (alleviation of) the disease condition is noted at an earlier time after administration of the composition of this invention than if the antibiotic or immune response-enhancing agent were administered alone and without administration of the other ingredient. On the other hand, where an administered antimicrobial composition of this invention contains an in vivo effective, but less than usual amount of antibiotic, and is followed by further relatively smaller doses of antibiotic, an improvement in (alleviation of) the host's disease condition can take about as long as is usual for the normally used dosage amount, but toxicity caused by the antibiotic is typically reduced.

More usually, an antimicrobial composition of this invention is administered to the host a plurality of times during a treatment period as is appropriate to the particular disease being treated, such as one to two weeks or one month. Such a plurality of admininstrations is also typically followed by a plurality of administrations of in vivo effective amounts of antibiotic, as described before. The results of such administrations are as described hereinbefore.

Single administrations or a plurality of administrations within a 24 hour period (1 day) of an antimicrobial composition typically provides a primary immune response to the antigens (immunogens) presented by the infecting pathogenic microorganism. Multiple administrations within a one month time period, or more preferably a one to about a two week time period, assists the host in mounting an anamnestic (memory) immune response to the immunogenic determinants borne by the infecting organism. Such multiple administrations also assist in providing non-specific immune responses such as the secretion of lysosomal enzymes by neutrophils that can attack bacteria and fungi.

The method of this invention can also be practiced by separate administrations of an in vivo effective amount of an antibiotic and a potentiating amount of an immune response-enhancing agent. Each active ingredient is typically administered as a unit dose dispersed in a physiologically tolerable carrier, as before discussed.

In this situation, it is important only that both active ingredients be present in the mammalian host at the same time. The in vivo effective and potentiating amounts of the respective active ingredients used and the results obtained are substantially the same as those discussed before. Typically, the potentiating dose of immune response-enhancing agent is administered within about 72 hours of the first dose of antibiotic, and preferably within about 24 hours of that first dose.

The host mammal having a microbial infection and to which an antimicrobial composition of this invention is administered is typically immunocompetent. That is, the host is not in an immunosuppressed or immunodeficient state, but merely has an infection.

However, the compositions and methods of this invention are also useful in hosts that are (1) immunosuppressed as can occur as a consequence of certain chronic infections, after receipt of immunosuppressive chemotherapy or radiation therapy, or (2) immunodeficient as are those patients who suffer from hypogammaglobulinemia. The compositions and methods of this invention are particularly useful in such hosts because it can bolster their natural immune defenses, which are otherwise immunocompromised and permit relatively easy access for opportunistic infections.

D. Assay Procedures

The efficacy of an antimicrobial composition or method of this invention can be assayed in a number of ways. Laboratory animals such as inbred strains of laboratory rats and mice are typically used for such assays.

Exemplary strains of immunocompetent mice are CBA/CaJ, A/J and BALB/c. Exemplary immunodeficient mice include CBA/N and C3H/HeJ. $F_1$ and $F_2$ progeny of crosses between immunocompetent and immunodeficient strains are also useful for some assay procedures.

Useful inbred strains of laboratory mice are readily available from a number of commercial and governmental sources. For example, CBA/CaJ and CBA/N mice are available from Jackson Laboratory, Bar Harbor, ME.

In one assay procedure, study and control mice having a microbial infection induced by injection of a fixed number of microorganisms are administered an antimicrobial composition of this invention, either of its components singly, or a control composition, as appropriate. Blood, serum or any other body sample is taken from the animals and used to culture the infecting microbe by a usual technique for that pathogen. Comparisons of the amounts of culturable pathogen or another measurable function of the presence of pathogen from the various animals provides an assay for alleviation of the disease condition.

For example, Jayawardena et al., *J. Immunol.*, 123: 2532-2539 (1979) and Hunter et al., *J. Immunol.*, 123: 133-137 (1979) reported malarial infections using *P. yoelii* in $F_1$ hybrids between immunocompetent (BALB/cJ and C57BL/6J as well as DBA/2) mice and CBA/N mice that have an X-linked immune defect that is reported by Jayawardena et al. to be attributed to a maturational defect in or absence of a subset of B cells. Parasitemias measured by both groups from Giesma-stained thin blood films were used to follow the course of infection in the animals.

O'Brian et al., *J. Immunol.*, 123: 720-724 (1979) reported on the susceptibility of normal, $F_1$ and $F_2$ hybrids of normal and CBA/N mice to *Salmonella typhimurium*. Those workers determined $LD_{50}$ values at specified times after infection for a particular strain of *S. typhimurium* in each of the mouse strains they studied. Once such $LD_{50}$ values are obtained, disease alleviation using treatment regimens of a composition and method of the instant invention or either of its components singly are compared using differences in $LD_{50}$ of the infecting agent as the yardstick in the assay.

Another assay procedure is that of Suzuki and Senda, *J. Antibiotics*, Vol. XXXVIII: 249 (1985). In accordance with that procedure, test organisms are cultured in nutrient broth at 37 degrees C. for 16 hours with shaking. Mice are intraperitoneally injected with 0.5 ml of a microbial suspension in saline or in another vehicle. Inoculum sizes range from 10–15 times the minimal lethal dose for each microbe type used. Each study is designed so that all untreated mice die within three days after infection. Control compositions, antibiotics and immune response-enhancing agents are administered alone or together in accordance with a method of this invention. The administration is given subcutaneously once at different times before or after infection. $LD_{50}$ values are calculated by the Litchfield-Wilcoxon method 7 days after infection.

BEST MODE FOR CARRYING OUT THE INVENTION

Example 1

Tablets

Tablets useful for treating a *S. typhimurium* infection are compounded from the following ingredients:

|  | Parts by Weight |
| --- | --- |
| Chloramphenicol | 10.0 |
| 8-(1'-Beta-D-ribofuranosidyl)-isoxanthopterin | 5.0 |
| Lactose, powdered | 37.4 |
| Corn starch, dry | 32.5 |
| Finely divided $SiO_2$ | 5.6 |
| Polyvinylpyrrolidone | 0.6 |
| Magnesium stearate | 0.4 |
|  | 90.0 |

The chloramphenicol and isoxanthopterin derivative are thoroughly admixed with the lactose, 25.0 parts by weight of the corn starch, and 4.0 parts by weight of the $SiO_2$. The resulting admixture is then uniformly moistened with a 5% ethanolic solution of polyvinylpyrrolidone. The moist mass is then passed through a one-millimeter mesh screen to produce a granulate. The produced granulate is dried for about 24 hours at 60° C. in a drying chamber. The dried granulate is again passed through a one-millimeter mesh screen. The obtained granulate (80.0 parts) is admixed in a suitable mixer with a mixture consisting of the remainder of the $SiO_2$, the remainder of the corn starch and all of the magnesium stearate, which mixture previously had been passed through a one-millimeter mesh screen. The thus-obtained admixture is then pressed into tablets weighing 900 milligrams each and containing 100 milligrams of chloramphenicol and 50 milligrams of the isoxanthopterin admixed with the substantially inert carrier.

Example 2

Starch Capsules

Capsules for alleviating gram positive bacterial infections can contain ampicillin as an antibiotic active ingredient.

Capsule contents are compounded from the following ingredients:

|  | Parts by Weight |
| --- | --- |
| Ampicillin | 200.0 |
| 6-Carboxy-8-(1'-beta-D-glucopyranosidyl)-isoxanthopterin | 5.0 |
| Lactose | 700.0 |
| Corn Starch | 1094.5 |
|  | 2000.0 |

The ampicillin and isoxanthopterin derivative are gradually admixed with the lactose. When all of the lactose has been admixed, the obtained admixture is blended with the corn starch. The resulting blend is then filled into capsules holding 1.0 gram of the blend. Each capsule contains 100 milligrams of ampicillin along with 2.50 milligrams of the isoxanthoperin derivative.

Example 3

Tablets

Tablets, each containing 250 milligrams of sulfamethizole and 25 milligrams of 6-methyl-8-(1'-beta-D-2'-deoxyribofuranosidyl)isoxanthopterin, is prepared from the following types and amounts of ingredients:

|  | Parts by Weight |
| --- | --- |
| Sulfamethizole | 500 |
| 6-Methyl-8-(1'-beta-D-2'-deoxyribofuranosidyl)isoxanthopterin | 50 |
| Dicalcium Phosphate | 1000 |
| Methyl cellulose, U.S.P. (15 cps) | 75 |
| Corn Starch | 325 |
| Magnesium stearate | 50 |
|  | 2000 |

The sulfamethizole, isoxanthopterin derivative and dicalcium phosphate are mixed well, granulated with 7.5 percent solution of methyl cellulose in water, passed through a No. 8 screen (U.S. Standard Sieve Series) and dried carefully to form granules. The dried granules are passed through a No. 12 screen (U.S. Std. Sieve Series), mixed thoroughly with the starch and magnesium stearate, and compressed into tablets.

These tablets are useful against a wide spectrum of gram positive and gram negative bacteria when administered perorally at a dose of two to four tablets three to four times daily.

Example 4

Injectable Preparation

A sterile preparation suitable for intramuscular injection and containing 100 milligrams of cefazolin sodium and 25 milligrams of 6-carboxyethyl-8-(1'-beta-D-ribofuranosidyl)isoxanthopterin in each milliliter is prepared from the following types and amounts of ingredients:

| Cefazolin sodium | 100 grams |
| --- | --- |
| 6-Carboxyethyl-8-(1-beta-D-ribofuranosidyl)isoxanthopterin | 25 grams |
| Benzyl benzoate | 200 milliliters |
| Methylparaben | 1.5 grams |
| Propylparaben | 0.5 grams |

| | |
|---|---|
| -continued | |
| Cottonseed oil qs to | 1000 milliliters |

Two to five milliliters of this sterile preparation are injected every 8 to 12 hours to treat pneumococcal pneumonia or mild infections caused by gram positive cocci.

Example 5

Aqueous Preparation for Oral Use

An aqueous preparation for oral use containing in each 5 milliliters (1 teaspoon) 62.5 milligrams of dicloxacillin sodium and 5 milligrams of 8-chloroguanosine is prepared from the following ingredients:

| | |
|---|---|
| Dicloxacillin sodium | 12.5 grams |
| 8-Chloroguanosine | 1.0 grams |
| Methylparaben, U.S.P. | 0.75 grams |
| Propylparaben, U.S.P. | 0.25 grams |
| Saccharin sodium | 1.25 grams |
| Cyclamate sodium | 0.25 grams |
| Glycerin | 300 milliliters |
| Tragacanth powder | 1.0 grams |
| Orange oil flavor | 1.0 grams |
| F.D. and C. orange dye | 0.75 grams |
| Deionized water, q.s. to | 1000 milliliters |

A dose of one to about five teaspoons is taken every 6 hours for treating infections caused by penicillinase-producing bacterial strains such as *Staph. pyogenes* var. aureus.

Example 6

Injectable Solution

An injectable aqueous solution is prepared from the following ingredients:

| | Grams |
|---|---|
| Gentamicin sulfate | 4 |
| 7-Methyl-8-oxoguanosine | 4 |
| Benzyl alcohol NF | 0.9 |
| Water for injection qs to | 100 |

Aliquots of the above solution are injected to provide 0.5 milligrams per kilogram of body weight of each active ingredient at 8 hour intervals for 7–10 days for treatment of gram negative bacterial infections.

Example 7

Oral Suspension

An aqueous preparation for oral use in which each 5 milliliters contains 125 milligrams of nalidixic acid and 5 milligrams of 8-hydroxyguanosine is prepared from the following ingredients:

| | Grams |
|---|---|
| Nalidixic acid | 25.0 |
| 8-Hydroxyguanosine | 1.0 |
| Alcohol USP | 12.5 |
| Glycerin USP | 45.0 |
| Syrup USP | 20.0 |
| Flavorant qs | |
| Purified Water qs ad | 100.0 |

The oral preparation is administered in 20 milliliter aliquots four times per day to treat infections of pathogenic Enterobacteriacae.

Example 8

Repeat Antibiotic Administration in the Absence of an Immune Response-Enhancing Agent A starch capsule of Example 2 is administered. Thereafter, commercially available tableats containing 125 milligrams of ampicillin are administered to provide 125 milligrams of ampicillin to an adult human every 6 hours.

Example 9

Hard Gelatin Capsules

A lot of 1000 hard gelatin capsules each containing 165 milligrams of sulfoxone sodium and 85 milligrams of 7-oxa-8-oxoguanosine is prepared from the following ingredients:

| | Grams |
|---|---|
| Sulfoxone sodium | 165 grams |
| 7-Oxa-8-oxoguanosine | 85 grams |
| Starch, dried | 150 grams |
| Calcium stearate | 2 grams |
| Talc | 3 grams |

The above ingredients are mixed well and the resulting admixture is filled into two-piece hard gelatin capsules. The capsules are administered to treat leprosy at two per week for two weeks and at four per wek for the next two weeks. Thereafter, 330 milligrams per week of the sulfoxone sodium are administered daily for six days per week.

The present invention has been described with respect to preferred embodiments. It will be clear to those skilled in the art that modifications and/or variations of the disclosed subject matter can be made without departing from the scope of the invention set forth herein.

What is claimed is:

1. An antimicrobial composition comprising a diluent amount of a physiologically tolerable carrier admixed with two active ingredients, said active ingredients comprising (1) an effective amount of an antibiotic and (2) a potentiating amount of an immune response-enhancing agent, said agent having a structure that conforms to a formula selected from the group consisting of

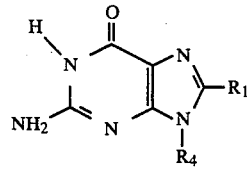

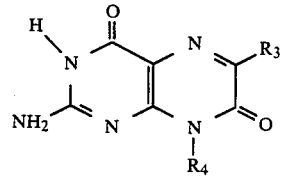

-continued

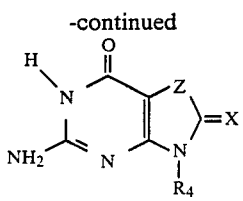

wherein
Z is N—$R_2$, O, or S;
$R_1$ contains fewer than about 15 atoms and has a Hammett substituent sigma constant for ionization of a meta-substituted benzoic acid that is greater than that of hydrogen;
$R_2$ is a radical selected from the group consisting of lower alkyl, lower beta-alkenyl, benzyl, hydroxy lower alkyl, polyhydroxy lower alkyl, lower alkylene lower alkylcarboxylate, lower alkanoyl, lower alkylcarboxy, lower alkoxy lower alkyl carbonyl, and lower alkyl carboxamido in which the carboxamido group has the formula $CONR_9R_{10}$ wherein $R_9$ and $R_{10}$ are the same or different and are selected from the group consisting of hydrogen and lower alkyl or $NR_9R_{10}$ together form a heterocyclic ring having five or six atoms in the ring;
X is oxygen or sulfur;
$R_3$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo, lower alkoxy, phenyl-lower alkoxy, halo, mercapto, thioxo, lower alkylthio, phenyl-lower alkylthio, lower alkanoyl, carboxy, lower alkoxy carbonyl, lower alkylcarboxy, lower alkylene lower alkylcarboxylate, lower alkoxy lower alkyl carbonyl, and lower alkyl carboxamido in which the carboxamido group has the formula $CONR_9R_{10}$ wherein $R_9$ and $R_{10}$ are the same or different and are selected from the group consisting of hydrogen and lower alkyl or $NR_9R_{10}$ together form a heterocyclic ring having five or six atoms in the ring;
$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent if present on one oxygen is present on all available ring substituent oxygens;
the pharmaceutically acceptable salts of said agent; and
the tautomers thereof.

2. The composition according to claim 1 wherein $R_4$ is the 1'-ribofuranosidyl radical.

3. The composition according to claim 2 wherein said immune response-enhancing agent has a structure that corresponds to the formula

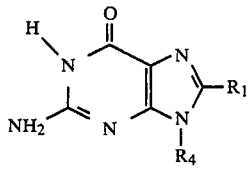

wherein $R_1$ is a radical selected from the group consisting of halo, hydroxy, mercapto, lower alkyl sulfide, lower alkyloylthio, nitro, cyano, lower alkoxy, halomethyl, carboxy, lower alkanoyl, trifluoromethyl, lower alkanamido, lower alkyl sulfonyl, sulfonamide and methylelenoxy lower alkyl ether.

4. The composition according to claim 2 wherein said immune response-enhancing agent has a structure that corresponds to the formula

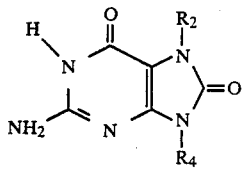

wherein $R_2$ is a radical selected from the group consisting of lower alkyl, lower beta-alkenyl and benzyl.

5. The composition according to claim 2 wherein said immune response-enhancing agent has a structure that corresponds to the formula

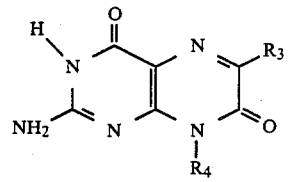

wherein $R_3$ is a radical selected from the group consisting of hydrogen, hydroxy, lower alkyl, carboxy, lower alkoxy carbonyl, and polyhydroxy lower alkyl.

6. The composition according to claim 2 wherein said immune response-enhancing agent is selected from the group consisting of 7-methyl-8-oxo-guanosine, 8-mercaptoguanosine, 7-allyl-8-oxoguanosine, 8-chloroguanosine, 8-bromoguanosine, 8-(1'-beta-D-ribofuranosidyl)isoxanthopterin, 6-methyl-8-(1'-beta-D-ribofuranosidyl)isoxanthopterin, 6-carboxy-8-(1'-beta-D-ribofuranosidyl)isoxanthopterin and 7-oxa-8-oxoguanosine.

7. A method of treating a microbial infection in a mammalian host comprising administering to said host two active ingredients, said active ingredients comprising (1) a unit dose of a composition that contains a diluent amount of a physiologicaly tolerable carrier admixed with an in vivo effective amount of an antibiotic and (2) a unit dose of a composition that contains a diluent amount of a physiologically tolerable carrier admixed with a potentiating amount of an immune response-enhancing agent, said antibiotic and said agent being administered to the host in the presence of each other in vivo, said agent having a structure that conforms to a formula selected from the group consisting of

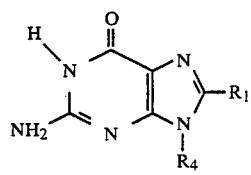

-continued

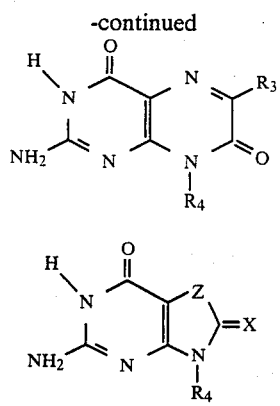

wherein

Z is N—R$_2$, O or S;

R$_1$ contains fewer than about 15 atoms and has a Hammett substituent sigma constant for ionization of a meta-substituted benzoic acid that is greater than that of hydrogen;

R$_2$ is a radical selected from the group consisting of lower alkyl, lower beta-alkenyl, benzyl, hydroxy lower alkyl, polyhydroxy lower alkyl, lower alkylene lower alkylcarboxylate, lower alkanoyl, lower alkylcarboxy, lower alkoxy lower alkyl carbonyl, and lower alkyl carboxamido in which the carboxamido group has the formula CONR$_9$R$_{10}$ wherein R$_9$ and R$_{10}$ are the same or different and are selected from the group consisting of hydrogen and lower alkyl or NR$_9$R$_{10}$ together form a heterocyclic ring having five or six atoms in the ring;

X is oxygen or sulfur;

R$_3$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo, lower alkoxy, phenyl-lower alkoxy, halo, mercapto, thioxo, lower alkylthio, phenyl-lower alkylthio, lower alkanoyl, carboxy, lower alkoxy carbonyl, lower alkylcarboxy, lower alkylene lower alkylcarboxylate, lower alkoxy lower alkyl carbonyl, and lower alkyl carboxamido in which the carboxamido group has the formula CONR$_9$R$_{10}$ wherein R$_9$ and R$_{10}$ are the same or different and are selected from the group consisting of hydrogen and lower alkyl or NR$_9$R$_{10}$ together form a heterocyclic ring having five or six atoms in the ring;

R$_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent if present on one oxygen is present on all available ring substituent oxygens;

the pharmaceutically acceptable salts of said agent; and the tautomers thereof.

8. The method according to claim 7 wherein said in vivo effective amount of antibiotic and said potentiating amount of immune response-enhancing agent are contained in a single, antimicrobial composition.

9. The method according to claim 8 wherein said unit dose is administered perorally.

10. The method according to claim 8 wherein said unit dose is administered parenterally.

11. The method according to claim 8 wherein said microbial infection is due to pathogenic bacteria.

12. The method according to claim 8 wherein said microbial infection is due to pathogenic fungi.

13. The method according to claim 8 comprising the additional steps of administering said antimicrobial composition a plurality of times within a time period of about one month.

14. The method according to claim 8 comprising the additional steps of administering further unit doses of a second composition that contains an effective amount of said antibiotic, said further administrations occurring within a time period of about one month.

15. The method according to claim 8 wherein said mammalian host is in an immunosuppressed or immunodeficient state at the time of said administration.

16. The method according to claim 8 wherein R$_4$ is the 1'-ribofuranosidyl radical.

17. The method according to claim 16 wherein said immune response-enhancing agent has a structure that corresponds to the formula

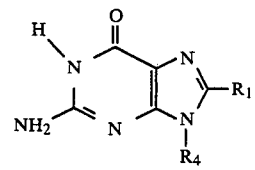

wherein R$_1$ is a radical selected from the group consisting of halo, hydroxy, mercapto, lower alkyl sulfide, lower alkyloylthio, nitro, cyano, lower alkoxy, halomethyl, carboxy, lower alkanoyl, trifluoromethyl, lower alkanamido, lower alkyl, sulfonyl sulfonamide and methylelenoxy lower alkyl ether.

18. The method according to claim 16 wherein said immune response-enhancing agent has a structure that corresponds to the formula

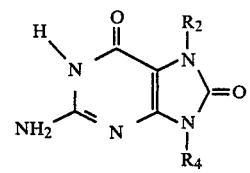

wherein R$_2$ is a radical selected from the group consisting of lower alkyl, lower beta-alkenyl and benzyl.

19. The method according to claim 16 wherein said immune response-enhancing agent has a structure that corresponds to the formula

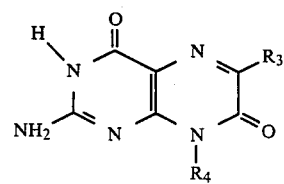

wherein R$_3$ is a radical selected from the group consisting of hydrogen, hydroxy, lower alkyl, carboxy, lower alkoxy carbonyl, and polyhydroxy lower alkyl.

20. The method according to claim 16 wherein said immune response-enhancing agent is selected from the group consisting of 7-methyl-8-oxo-guanosine, 8-mercaptoguanosine, 8-chloroguanosine, 7-allyl-8-oxoguanosine, 8-bromoguanosine, 8-(1'-beta-D-ribofuranosidyl)isoxanthopterin, 6-methyl-8-(1'-beta-D-ribofuranosidyl)isoxanthopterin 6-carboxy-8-(1'-beta-D-ribofuranosidyl)-isoxanthopterin and 7-oxa-8-oxoguanosine.

21. An antimicrobial composition comprising a diluent amount of a physiologically tolerable carrier admixed with two active ingredients, said actaive ingredients comprising (1) an effective amount of an antibiotic and (2) a potentiating amount of an immune response-enhancing agent, said agent having a structure that conforms to a formula selected from the group consisting of

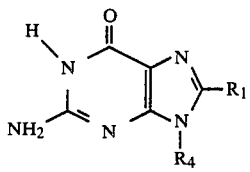

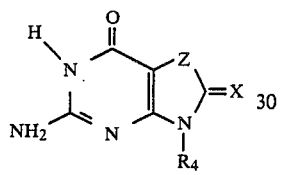

wherein
Z is N—$R_2$, O, or S;
$R_1$ contains fewer than about 15 atoms and has a Hammett substituent sigma constant for ionization of a meta-substituted benzoic acid that is greater than that of hydrogen;
$R_2$ is a radical selected from the group consisting of lower alkyl, lower beta-alkenyl, benzyl, hydroxy lower alkyl, polyhydroxy lower alkyl, lower alkylene lower alkylcarboxylate, lower alkanoyl, lower alkylcarboxy, lower alkoxy lower alkyl carbonyl, and lower alkyl carboxamido in which the carboxamido group has the formula $CONR_9R_{10}$ wherein $R_9$ and $R_{10}$ are the same or different and are selected from the group consisting of hydrogen and lower alkyl or $NR_9R_{10}$ together form a heterocyclic ring having five or six atoms in the ring;
X is oxygen or sulfur;
$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent if present on one oxygen is present on all available ring substituent oxygens;
the pharmaceutically acceptable salts of said agent; and
the tautomers thereof.

22. The composition according to claim 21 wherein $R_4$ is the 1'-ribofuranosidyl radical.

23. The composition according to claim 22 wherein said immune response-enhancing agent has a structure that corresponds to the formula

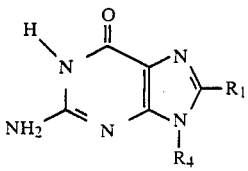

wherein $R_1$ is a radical selected from the group consisting of halo, hydroxy, mercapto, lower alkyl sulfide, lower alkyloylthio, nitro, cyano, lower alkoxy, halomethyl, carboxy, lower alkanoyl, trifluoromethyl, lower alkanamido, lower alkyl sulfonyl, sulfonamide and methylelenoxy lower alkyl ether.

24. The composition according to claim 22 wherein said immune response-enhancing agent has a structure that corresponds to the formula

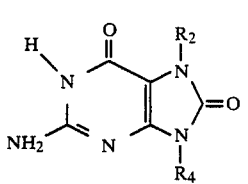

wherein $R_2$ is a radical selected from the group consisting of lower alkyl, lower beta-alkenyl and benzyl.

25. The composition according to claim 22 wherein said immune response-enhancing agent is selected from the group consisting of 7-methyl-8-oxo-guanosine, 8-mercaptoguanosine, 7-allyl-8-oxoguanosine, 8-chloroguanosine, 8-bromoguanosine, and 7-oxa-8-oxoguanosine.

26. A method of treating a microbial infection in a mammalian host comprising administering to said host two active ingredients, said active ingredients comprising (1) a unit dose of a composition that contains a diluent amount of a physiologicaly tolerable carrier admixed with an in vivo effective amount of an antibiotic and (2) a unit dose of a composition that contains a diluent amount of a physiologically tolerable carrier admixed with a potentiating amount of an immune response-enhancing agent, said antibiotic and said agent being administered to the host in the presence of each other in vivo, said agent having a structure that conforms to a formula selected from the group consisting of

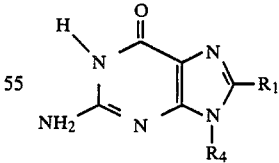

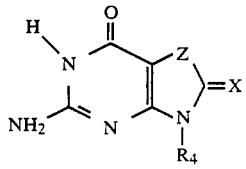

wherein
Z is N—$R_2$, O or S;

R₁ contains fewer than about 15 atoms and has a Hammett substituent sigma constant for ionization of a meta-substituted benzoic acid that is greater than that of hydrogen;

R₂ is a radical selected from the group consisting of lower alkyl, lower beta-alkenyl, benzyl, hydroxy lower alkyl, polyhydroxy lower alkyl, lower alkylene lower alkylcarboxylate, lower alkanoyl, lower alkylcarboxy, lower alkoxy lower alkyl carbonyl, and lower alkyl carboxamido in which the carboxamido group has the formula CONR₉R₁₀ wherein R₉ and R₁₀ are the same or different and are selected from the group consisting of hydrogen and lower alkyl or NR₉R₁₀ together form a heterocyclic ring having five or six atoms in the ring;

X is oxygen or sulfur;

R₄ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent if present on one oxygen is present on all available ring substituent oxygens;

the pharmaceutically acceptable salts of said agent; and the tautomers thereof.

27. The method according to claim 26 wherein said in vivo effective amount of antibiotic and said potentiating amount of immune response-enhancing agent are contained in a single, antimicrobial composition.

28. The method according to claim 27 wherein said unit dose is administered perorally.

29. The method according to claim 27 wherein said unit dose is administered parenterally.

30. The method according to claim 27 wherein said microbial infection is due to pathogenic bacteria.

31. The method according to claim 27 wherein said microbial infection is due to pathogenic fungi.

32. The method according to claim 27 comprising the additional steps of administering said antimicrobial composition a plurality of times within a time period of about one month.

33. The method according to claim 27 comprising the additional steps of administering further unit doses of a second composition that contains an effective amount of said antibiotic; said further administrations occurring within a time period of about one month.

34. The method according to claim 27 wherein said mammalian host is in an immunosuppressed or immunodeficient state at the time of said administration.

35. The method according to claim 27 wherein R₄ is the 1'-ribofuranosidyl radical.

36. The method according to claim 35 wherein said immune response-enhancing agent has a structure that corresponds to the formula

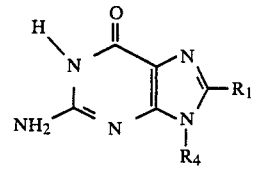

wherein R₁ is a radical selected from the group consisting of halo, hydroxy, mercapto, lower alkyl sulfide, lower alkyloylthio, nitro, cyano, lower alkoxy, halomethyl, carboxy, lower alkanoyl, trifluoromethyl, lower alkanamido, lower alkyl, sulfonyl sulfonamide and methylelenoxy lower alkyl ether.

37. The method according to claim 35 wherein said immune response-enhancing agent has a structure that corresponds to the formula

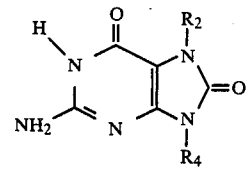

wherein R₂ is a radical selected from the group consisting of lower alkyl, lower beta-alkenyl and benzyl.

38. The method according to claim 35 wherein said immune response-enhancing agent is selected from the group consisting of 7-methyl-8-oxo-guanosine, 8-mercaptoguanosine, 8-chloroguanosine, 7-allyl-8-oxoguanosine, 8-bromoguanosine, and 7-oxa-8-oxoguanosine.

* * * * *